United States Patent [19]

Ramakrishnan

[11] Patent Number: 5,284,952
[45] Date of Patent: Feb. 8, 1994

[54] SULFONYL SUBSTITUTED CHEMILUMINESCENT LABELS AND THEIR CONJUGATES, AND ASSAYS THEREFROM

[75] Inventor: Kastooriranganathan Ramakrishnan, Eden Prairie, Minn.

[73] Assignee: London Diagnostics, Inc., Eden Prairie, Minn.

[21] Appl. No.: 859,995

[22] Filed: Mar. 30, 1992

Related U.S. Application Data

[63] Continuation-in-part of Ser. No. 140,040, Dec. 31, 1987, abandoned, and a continuation-in-part of Ser. No. 291,843, Dec. 29, 1988, abandoned, and a continuation-in-part of Ser. No. 418,956, Oct. 10, 1989, abandoned.

[51] Int. Cl.⁵ .......................................... C07D 219/04
[52] U.S. Cl. .................... 546/104; 436/501; 530/409; 544/355; 546/61; 546/79; 546/93; 546/102; 546/107; 546/108; 546/112; 546/147; 546/170; 548/309.4
[58] Field of Search .............. 546/79, 93, 107, 104, 546/107, 108, 309.4, 61, 112, 147, 170; 436/501; 530/409; 544/355; 548/309.4

[56] References Cited

U.S. PATENT DOCUMENTS

| | | | |
|---|---|---|---|
| 3,352,791 | 11/1967 | Sheehan et al. | 546/102 X |
| 3,689,391 | 9/1972 | Ullman | 546/102 X |
| 4,745,181 | 5/1988 | Law et al. | 546/104 X |
| 4,918,192 | 4/1990 | Law et al. | 546/104 |
| 4,946,958 | 8/1990 | Campbell et al. | 546/104 |
| 4,950,613 | 8/1990 | Arnold et al. | 546/104 |
| 5,110,932 | 5/1992 | Law et al. | 546/102 |

FOREIGN PATENT DOCUMENTS

| | | | |
|---|---|---|---|
| 216553 | 4/1987 | European Pat. Off. | 546/102 |
| 324202 | 7/1989 | European Pat. Off. | 546/102 |
| 330050 | 8/1989 | European Pat. Off. | 546/104 |
| 361817 | 4/1990 | European Pat. Off. | 546/102 |
| 1461877 | 1/1977 | United Kingdom | 546/102 |

*Primary Examiner*—Richard L. Raymond
*Attorney, Agent, or Firm*—George A. Skoler

[57] ABSTRACT

A chemiluminescent labeling composition comprising an ester, thioester or amide covalently and jointly bonded to (1) a carbon of a heterocyclic ring or ring system that is susceptible to attack by peroxide or molecular oxygen and (2) an aryl ring or ring system wherein the heterocyclic ring or ring system is distinquished by a heteroatom thereof in an oxidation state which causes the attacked carbon atom to form an intermediate that decays and produces chemiluminescence; the aryl ring or ring system contains at least three substituents on a six-member aromatic hydrocarbon that together sterically and electronically hinder hydrolysis of the linkage, which substituents involve ortho substituent groups on the aryl in conjunction with meta and-/or para —SO₂— substituents thereon. Included are the chemiluminescent labeling composition conjugated with a specific binding material; a chemiluminescent assay comprising the conjugate; and a chemiluminescent assay kit comprising the conjugate with the capability of conducting the assay.

18 Claims, No Drawings

SULFONYL SUBSTITUTED CHEMILUMINESCENT LABELS AND THEIR CONJUGATES, AND ASSAYS THEREFROM

RELATED APPLICATIONS

This application is a continuation-in-part of application Ser. No. 140,040, filed Dec. 31, 1987, now abandoned copending application Ser. No. 291,843, filed Dec. 29, 1988, now abandoned, and copending application Ser. No. 418,956, filed Oct. 10, 1989, now abandoned.

BRIEF DESCRIPTION OF THE INVENTION

This invention relates to unique chemiluminescent labeling compounds, conjugates containing associated versions of the labeling compounds, assays and kits for performing such assay utilizing the conjugates. The labeling compounds contain special halosulfonyl substituted aryl heterocyclic esters, thiolesters and amides, and their conjugate reaction products to form stable $-SO_2-$ containing structures.

BACKGROUND TO THE INVENTION

The literature describes classes of compounds that give off light or "luminesce" by reaction through chemical treatment. The compounds that have this capability are termed chemiluminescent materials. Their dissociation is typically caused by treatment with peroxide or molecular oxygen at high pH. Light is produced by the decay of the transient ("intermediate") structure formed by peroxide or molecular oxygen reaction at an $sp^2$ or $sp^3$ hybridized carbon in the compound that is part of a chain or a ring or ring system.

As the literature indicates, any series of reactions which produce the intermediate:

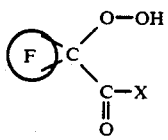

will lead to moderate to strong chemiluminescence. (F) is a structure such that the product carbonyl derivative

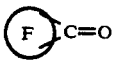

is fluorescent and X is a good leaving group, usually with XH, for efficient chemiluminescence, having a $pK_a$ of about $\leq 11$, preferably $<11$, and most preferably, from about 5 to about 8. The reaction may require base catalysis. The intermediate can be prepared (in isolable or transient form, depending on (F)) from species such as:

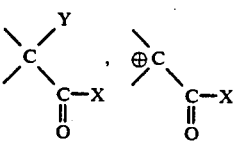

and $H_2O_2$ (Y is halogen, $-OSO_2R$, and the like) or

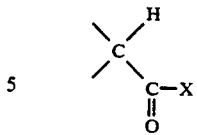

and base/$O_2$.

See Endeavour, 23, No. 117 (1973) p. 140, *The Chemistry of Bioluminescence* in "Bioluminescence in Action" (P. J. Herring, ed.), Academic Press, London, 1978 (pp. 64-5), *Proc. R. Soc. Lond.*, B 215, p. 256 (1982), *Progress in Organic Chemistry*, (W. Carruthers and J. K. Sutherland, eds.), Butterworth, London (1973), p. 261, all authored by F. McCapra.

For example, chemiluminescent aryl esters that contain such hybridized carbon, termed a labeling compound, react according to the following general reaction:

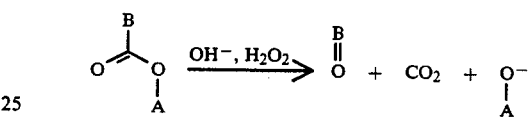

where A is an aryl ring or ring system and B is a heterocyclic ring or ring system. In this reaction, $-O-A$, the leaving group, is cleaved by perhydrolysis resulting in steps leading to the transient intermediate, $B=O$, that proceeds to decay generating luminescence.

The characteristics of some of these chemiluminescent compounds, their chemistry of manufacture, and other factors relating to them, are more fully described by McCapra, "Chemiluminescence of Organic Compounds," in Progress in Organic Chemistry, vol. 8, Carruthers and Sutherland ed., Wiley & Sons (1973); Kohen, Bayer, Wilechek, Barnard, Kim, Colleins, Beheshti, Richardson and McCapra, "Development Of Luminescence-Based Immunoassays For Haptens And For Peptide Hormones," pp. 149-158, in *Analytical Applications Of Bioluminescence and Chemiluminescence*, Academic Press, Inc. (1984); Richardson, Kim, Barnard, Collins and McCapra, *Clinical Chemistry*, vol. 31, no. 10, pp. 1664-1668 (1985); McCapra, "The Application of Chemiluminescence in Diagnostics," 40th Conference of the American Association of Clinical Chemists, New Orleans, La., Jul. 28, 1988; McCapra, "The Chemiluminescence Of Organic Compounds," Quarterly Reviews, vol. 20, pp. 485-510 (1966); McCapra, "The Chemiluminescence Of Organic Compounds," *Pure and Applied Chemistry*, vol. 24, pp. 611-629 (1970); McCapra, "The chemistry of bioluminescence," *Proceedings Of Royal Society*, vol. B215, pp. 247-278 (1982); McCapra and Beheshti, "Selected Chemical Reactions That Produce Light," *Bioluminescence and Chemiluminescence: Instruments and Applications*, CRC Press, vol. 1, Chapter 2, pp. 9-37 (1985); McCapra, "Chemiluminescent Reactions of Acridines," Chapt. IX, *Acridines*, R. M. Acheson, Ed., pp. 615-630, John Wiley & Sons, Inc. (1973); McCapra, "Chemical Mechanisms in Bioluminescence," *Accounts Of Chemical Research*, vol. 9, no. 6, pp. 201-208 (June 1976); and in many other publications and presentations on the subject.

As noted in the above literature, chemiluminescent compounds of a variety of structures have been projected as labels for a variety of assays including immunoassays (in this respect, see U.S. Pat. Nos. 4,383,031, 4,380,580 and 4,226,993). The esters, thiolesters and amides, alone or conjugated (i.e., chemically coupled to another material), are especially desirable forms of chemiluminescent labels. However, they lose their luminescence capability over time in an aqueous system because they hydrolyze to products that are not available to the assay. Until recently, these compounds have not been used in commercial assays. Until this invention, the ester, thiolester and amide forms of this class of materials lacked sufficient hydrolytic stability to be stored in the most convenient form over an extended period of time, which is as a component of an aqueous system.

The sensitivity of an assay is a measure of its ability to find a component present at low concentrations in the sample. The smaller the concentration in the sample being analyzed, the more sensitive is the assay if it is capable of measuring to that concentration. As pointed out by Spencer et al., *Thyroid Today*, vol. XIII, no. 4, 4th Q. 1990, a new category of sensitivity in immunometric assay (IMA) of TSH has been created as a result of the introduction of the chemiluminescent labels, conjugates, assays and kits of this invention. Chemiluminescent labels of this invention have been on sale as of about August 1988, and they have received critical acclaim by those in the art for unique sensitivity. Prior to this invention, sensitivity of TSH IMA was rated as "sensitive," "ultrasensitive" and "supersensitive." There was thereafter developed a generational classification, such as 1st generation assays, 2nd generation assays and 3rd generation assays, leaving open the possibility for later generations. The only IMA that is rated as a third generation IMA is the assay encompassed by this invention. As the authors stated:

"Appropriately, third generation TSH IMAs,[4,5] display a further tenfold improvement in functional sensitivity, with an assay limit of 0.01 to 0.02 mU/L."

Ross, *Clinical Chemistry News*, Vol. 15, No. 11, entitled "New Assays Reveal TSH Deviations" states:

"Most s-TSH immunometric assays (IMA) are excellent at discriminating TSH levels that are normal from those consistent with hyperthyroidism. However, the detection limit of these assays has generally been only slightly less than the lower limit of the euthyroid range, so that the measurement of subnormal but detectable TSH concentrations has been limited.

"A new commercially available chemiluminescent assay (London Diagnostics) has an eight- to 10-fold increase in sensitivity over commercially available IMAs. The lower detection limits of so-called third-generation assays such as this one will allow partial suppression to be discriminated from more complete thyrotrope suppression. For example, a recent study found that half of the patients taking suppressive doses of levothyroxine who had an undetectable value in an s-TSH IMA had a detectable value in the more sensitive chemiluminescent assay."

The uniqueness of the chemiluminescent labels of the invention to achieve more sensitive IMA or immunochemiluminometric assay (ICMA) is discussed by Spencer et al., "Application of a New chemiluminometric Thyrotropin Assay to Subnormal Measurements," *Journal of Clinical Endocrinology and Metabolism*, Vol. 70, No. 2, pp. 453-460 (1990).

It is well understood in chemistry that carboxylic acid esters, thiolesters and amides are susceptable to hydrolytic attack under acidic or basic conditions resulting in the formation of the carboxylic acid and the hydroxy, mercapto or amino component that is the theoretical or actual precursor to the ester, thiolester or amide. Hydrolysis is more pronounced under greater acidity or basicity. It is also recognized in chemistry that certain levels of hydrolysis can be inhibited by the inclusion of bulky groups that chemically sterically hinder those linkages, see Nishioka, et al., *J. Org. Chem.*, vol. 40, no. 17, pp. 2520-2525 (1975), Fujita et al., "The Analysis of the Ortho Effect," *Progress in Physical Organic Chemistry*, 8, pp. 49-89 (1976), and Morrison and Boyd, *Organic Chemistry*, 5th Ed., pp. 842-843 (1987) and March, *Advanced Organic Chemistry*, 3rd Ed., page 240 (1985). According to March:

"Another example of steric hindrance is found in 2,6-disubstituted benzoic acids, which are difficult to esterify no matter what the resonance or field effects of the groups in the 2 or the 6 position. Similarly, once the 2,6-disubstituted benzoic acids are esterified, the esters are difficult to hydrolyze." (Emphasis in the original)

The difficulty in esterification is not the same in making esters from 2,6-substituted phenols, but the general principles described by March are applicable to enhancing the hydrolytic stability of the resultant ester so long as the ortho substitutions are electron donating. As this invention demonstrates, effective levels of hydrolytic stability require the presence of a select level of electron withdrawing chemical effect in conjunction with (and in addition to) traditional chemical steric hindrance factors.

As this invention demonstrates, effective levels of hydrolytic stability and sensitivity of chemiluminescent labeled conjugates utilized for ICMA are materially enhanced by the presence of a halosulfonyl in the label compound and sulfonamide in the conjugate utilized in the ICMA.

The functional electron withdrawing or electron donating characteristics of a group in an organic compound is conventionally measured relative to hydrogen. This relative ranking accepts that all groups on a molecule will provide some electron withdrawing effect, and distinquishes them by the nature of impact the group has on the molecule's performance. An electron withdrawing functional group, characterized by a positive number, will draw electrons to itself more than hydrogen would if it occupied the same position in the molecule. The opposite occurs with an "electron donating group," a lesser electron withdrawing group which chemical convention characterizes by a negative number. Sigma para values ($\sigma_p$) are the relative measurement of electron withdrawing or electron donating qualities of a functional group in the para position on benzoic acid. See March, *Advanced Organic Chemistry*, 3rd Edition, Publ. by John Wiley & Sons, New York, N.Y. (1985) at pp. 242-250 and 617-8. Tables of $\sigma_p$ values for various groups can be found in Hansch et al., *J. Med. Chem.* 16(11): 1209-1213 (1973) and Hansch and Leo, "Substituent Constants for Correlation Analysis in Chemistry and Biology," Ch. 6, pp. 49-52 (John Wiley & Sons, New York 1979). The $\sigma_p$ values reported in the Hansch articles are relied on herein in characterizing relative values for groups both in the meta and para position.

The function of chemiluminescent labels in assay applications involves the coupling of the label compound to a substrate molecule. Such coupling can be achieved by solvent interraction (e.g., molecular compatibility), any heterolytic or homolytic mechanism induced by chemical means and influenced by physical effects, such as time, temperature and/or mass action. For example, the reaction can be nucleophilic or electrophilic, or it can involve free radical mechanisms. In the broadest perspective, the coupling can be viewed as achievable via strong to weak bonding forces.

A chemiluminescent label in assays is an associated moiety of a binding material. The moiety is derived from a chemical compound which, as such, possesses chemiluminescent capabilities. Hereinafter, the term moiety as applied to the label as such, is a reference to the compound prior to being associated with a binding material. The term associated is intended to include all or any of the mechanisms for coupling the label to the substrate molecule.

The term "functional" in chemistry typically refers to a group that influences the performance of a chemical or constitutes the site for homolytic or heterolytic reactions. For example, a functional alkyl substituent, used in the context of interreactions through that substituent, means an alkyl group substituted so that it can effect that reaction. But an alkyl group termed functional for the electronic effects it induces in the molecule is a reference to the alkyl group per se.

THE INVENTION

This invention relates to unique chemiluminescent labeling compounds, conjugates containing associated versions of the labeling compounds, assays and kits for performing such assay utilizing the conjugates. The labeling compounds contain special —$SO_2$— substituted aryl heterocyclo esters, thiolesters and amides.

The root compound of the invention is a chemiluminescent compound characterized by the presence a substituted —$SO_2$— aryl ester, thiolester or amide of a carboxylic acid substituted heterocyclic ring that is susceptible to chemical attack (such as by oxidic attack) to dissociate the heterocyclic ring to form a transient compound. The heterocyclic ring is ring carbon-bonded to the carbonyl of the ester, thiolester and amide moiety and possesses a heteroatom in an oxidation state that allows chemiluminescence by dissociating a compound ("intermediate") that decays to produce chemiluminescence, at the carbon bonded to the carbonyl. The aryl ring or ring system is ring carbon-bonded to the oxygen, sulfur or nitrogen of the ester, thiolester or amide, as the case may be, and contains at least three substituents on a six-member ring. The substitution on the six-member ring comprises diortho electron donating substitution and meta and/or para —$SO_2$— substitution on the aryl unit that is bonded thereto by a sulfur to aryl ring carbon covalent bond.[1]

[1]This structure is to be contrasted with the structure: —$OSO_2F$; a structure obtained by the reaction of, e.g., $C_6H_5O^-$ with $SO_2F_2$ (see Cotton and Wilkinson, *Advanced Inorganic Chemistry*, 5th Ed., page 518 (1988).

Also in accordance with the present invention are conjugates of the labeling composition, assay systems utilizing the conjugates, and assay kits incorporating such chemiluminescent labels.

In particular, this invention relates to a hydrolytically stable heterocyclic composition capable of chemiluminescent properties when labeled (i.e., affixed as a label) to a specific binding material by chemically-induced dissociation, comprising (a) an aryl ring, (b) a sterically-hindered ester, thiolester or amide linkage moiety with enhanced hydrolytic stability, and (c) a heterocyclic organic ring moiety, in which (1) the carbonyl carbon of (b) is covalently bonded to a carbon atom (x) of (c) and the remaining free valence of (b) is carbon bonded to an aromatic ring carbon atom (y) of (a), (2) (a) contains at least three substituent groups hindering hydrolysis of (b), two of which are electron donating and located on the ring carbon atoms adjacent to (y), the remainder includes a —$SO_2$— containing group located meta or para to (y), and (3) (c) contains a ring member heteroatom in an oxidation state that provides such chemiluminescence properties.

Also, this invention contemplates hydrolytically stable conjugates possessing chemiluminescent properties by chemical dissociation, comprising a chemiluminescent label bonded to a specific binding material that contains (a) an aryl ring, (b) a sterically-hindered ester, thiolester or amide linkage moiety with enhanced hydrolytic stability, and (c) a heterocyclic organic ring moiety, in which (1) the carbonyl carbon of (b) is covalently bonded to a carbon atom (x) of (c) and the remaining free valence of (b) is carbon bonded to an aromatic ring carbon atom (y) of (a), (2) (a) contains at least three substituent groups hindering hydrolysis of (b), two of which are electron donating and located on the ring carbon atoms adjacent to (y), the remainder includes a meta and/or para —$SO_2$— bonded to the specific binding material, and (3) (c) contains a ring member heteroatom that is in an oxidation state whereby reaction of molecular oxygen or a peroxide with said composition forms an intermediate which decays to produce chemiluminescence.

The invention encompasses a method for assaying the presence of an analyte in a sample. The method comprises contacting an analyte with the aforementioned chemiluminescent-labeled specific binding material (the "conjugate"), inducing chemiluminescence by decay of an intermediate dissociated from the conjugate, and measuring luminescence therefrom to assay the analyte.

In keeping with the inventive chemiluminescent-label's function of assaying, the invention embodies a specific binding assay kit comprising a vial containing a conjugate possessing chemiluminescent properties by chemically induced dissociation and containing the aforementioned chemiluminescent label bonded to a specific binding material.

The invention recognizes that hydrolytic stability of a chemiluminescent label composition that utilizes aryl ester, thiolesters, and amides, as defined herein, linked to heterocyclic carboxy compounds, is affected by two factors. The first is the utilization of diortho substitution on the aryl ring of a kind that traditionally contributes to hydrolytic stability. This the "bulky group" steric hindrance effect noted by Morrison and Boyd, supra. In the context of para sigma values, these bulky groups are typically classed as electron donating. The second is the utilization of meta and/or para substitution on the same ring that untraditionally contributes to hydrolytic stability. This latter substitution possesses a —SO₂— bonded to the ring. This combination of groups provides enhanced hydrolytic stability to the labeling composition.

In addition, this invention relates to chemiluminescent labels that the art recognizes to provide the only known third generation TSH ICMAs. Thus, the invention in chemiluminescent labels and chemiluminescent labeled conjugates couples exceptional hydrolytic stability with unpredictably sensitive ICMAs.

In a preferred embodiment, the invention relates to the two specific chemiluminescent label compounds of the invention that are utilized in the aforementioned third generation TSH ICMAs. These chemiluminescent label compounds have provided products that have met commercial success and effect assay sensitivities that have created a whole new classification for TSH IMAs. In addition, these two chemiluminescent label compounds have been effective in other ICMA assays showing performance characteristics as good as, if not better than, other IMAs based on chemiluminescence or other detection means. The two labels are

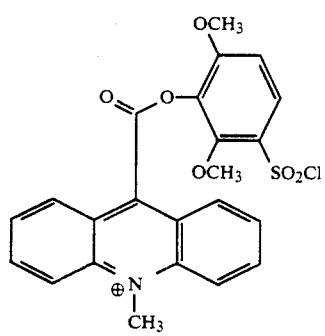

(2,6-dimethoxy-3-chlorosulfonyl)-phenyl-
N-methyl-acridinium-9-carboxylate and

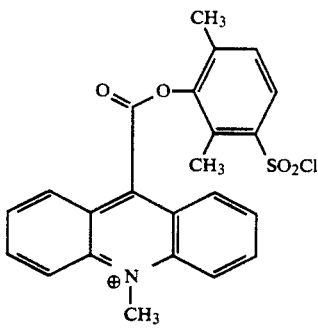

(2,6-dimethyl-3-chlorosulfonyl)-phenyl-
N-methyl-acridinium-9-carboxylate

The invention relates to the reaction product of these labels with specific binding materials, particularly proteins, to form sulfonamides characterized by the following structures:

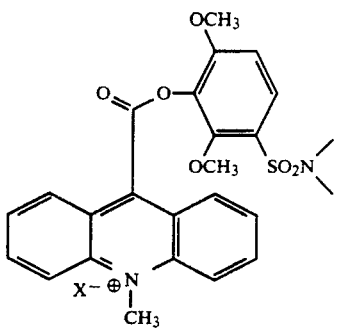

and

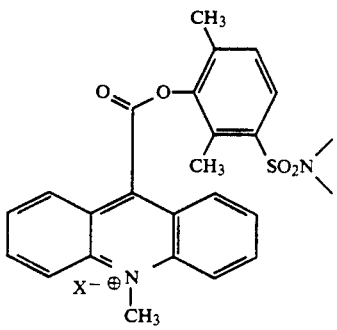

In the above formulae, at least one free valence of the nitrogen is bonded to carbon of an organic group or compound, and any remaining free valence is bonded to hydrogen.

DETAILED DESCRIPTION OF THE INVENTION

Desirable chemiluminescent labeling compounds of the present invention include compositions encompassed by the following formula:

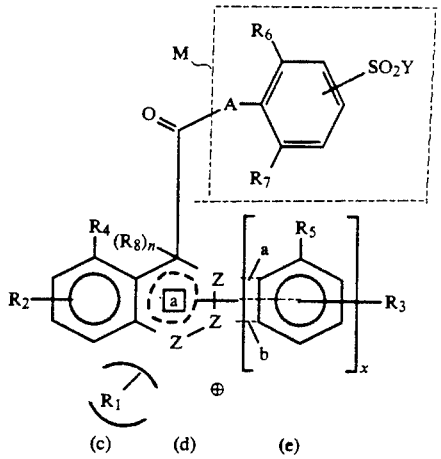

Formula "AB"

In this formula AB, [a] denotes the optional saturated or unsaturated nature of the internal heterocyclic ring shown in hatched lines. When n is 1, [a] is characterized by saturation, in which the ring in question is devoid of aromatic unsaturation. When n is 0, [a] is characterized by unsaturation, in which the ring in question is aromatically unsaturated. That distinction in unsaturation is further characterized by the following:

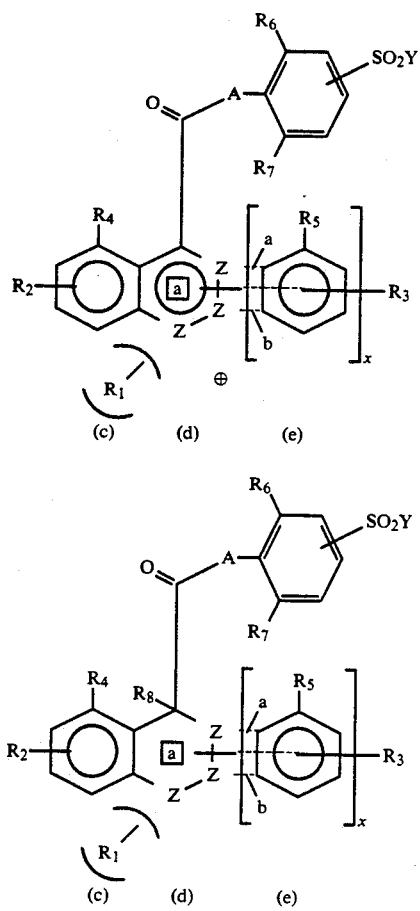

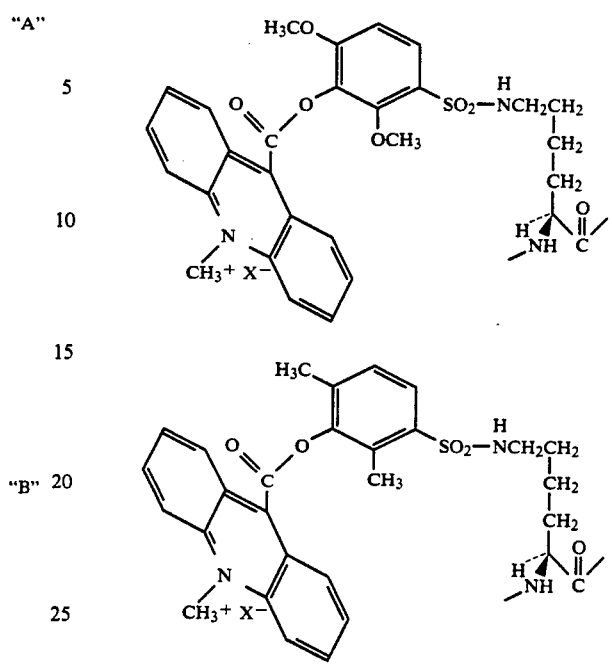

In the above formulae "A" and "B", [a] characterizes specific unsaturated (formula "A") or saturated (formula "B") forms. R$_8$ may be hydrogen. Formulas AB, as well as A and B, depict ring systems comprising at least two fused rings; in this case, rings designated "(c)", "(d)" and optionally "(e)". Two (2) of the Z's are carbon, and one (1) Z is nitrogen. Where the Z is carbon, it is bonded to one hydrogen unless it is part of a fused ring or contains a pendant group. Ring (e) may be a fused ring, in which case bonds a and b represent common carbons shared by both rings (d) and (e) and the proximate or adjacent Z's represent the shared carbons. Ring (e) may be a pendant ring attached to ring (d) by a convalent carbon to carbon bond represented by bonds a or b, depending upon where the pendancy occurs. The presence of ring (e) is determined by the value of x, which is either 0 or 1. M characterizes the leaving group even if the moiety is conjugated to a specific binding material. The leaving group possesses the typical pK$_a$ of about ≦11.

Y in the formulae may be halogen, such as chlorine, bromine, fluorine and iodine, with chlorine preferred, or the residue of an active hydrogen containing compound, such as an amino group within a protein. This latter configuration is characterized in the following specific acridinium structures:

The nucleophilic reaction by which the sulfonyl halide structure of the invention are conjugated is the conventional reaction:

$$-SO_2Cl + HR \rightarrow -SO_2R + HCl$$

where the active hydrogen compound "HR" comprises such active hydrogen containing moieties such as amino, amido, hydroxyl, thiol, and the like.

"A", in the above formulas, may be —O—, —S— or —NT—. T is a stable nitrogen bonded group such as —SO$_2$CF$_3$, to form —N(SO$_2$CF$_3$)—, and equivalent groups. Methods for forming such —NT— groups are described by Maulding et al., "Chemiluminescence from Reactions of Electrophilic Oxamides with Hydrogen Peroxide and Fluorescent Compounds," *J. Org. Chem.*, 33, 1, 250–254, (1968); Tseng et al., *J. Org. Chem.*, 44, 4113 (1979); Mohan, U.S. Pat. No. 4,053,430; Tseng et al., European Pat. Appln. 811 003 69.8 (1981); and European Pat. Applns. Pub. Nos. 0 273 115 and 0 257 541.

One or both of R$_6$ and R$_7$ may be hydrogen so long as R$_4$ and/or R$_5$ are peri substitutions that cause peri interactions.[2] Preferably, both R$_6$ and R$_7$ are alkyl (C$_{1-4}$), alkoxy or alkyl sulfide, part of a fused ring system, with alkyl and alkoxy being preferred.

[2] Webster's Third New International Dictionary, Unabridged: "having substituents in or relating to positions 1 and 8 in two fused 6-membered rings (as in napthalene)"

Of the peri groups, R$_4$ and R$_5$ (when ring (e) is fused with ring (d)), both may be hydrogen or one of more of them may be otherwise substituted. For example, R$_4$ may be a bulky steric-hindering group and R$_5$ may be a bulky steric-hindering groups or hydrogen. Preferably, both are hydrogen, but they may both be steric-hindering groups. (R$_1$-) is an organo group that is carbon to nitrogen bonded to the Z that is nitrogen. R$_2$- and R$_3$- are organo groups or hydrogen bonded to ring carbon atoms of rings (c), (d) and (e), as the case may be. When R$_2$- or R$_3$- are organo groups, they are bonded to ring carbon, preferably by a carbon to carbon bond, carbon to oxygen bond, carbon to nitrogen bond, carbon to sulfur bond, and the like. In addition, $R_2$-and $R_3$-may be amino, substituted amino, hydroxy, halogen, carboxy, or sulfonyl (and their esters).

Peri substituents, which can cause peri-interactions, include any group which can cause steric hindrance with respect to the carbon to which the ester, thiolester or amide linkage is attached and/or with respect to the carbon within the ester, thiolester of amide linkage. Preferred peri substituents include short alkyl groups (such as $C_{1-4}$, e.g., methyl, ethyl, and the like), aryl groups (e.g., phenyl), alkaryl (e.g., tolyl, xylyl, and the like), alkoxyalkyl (such as $C_{1-4}$ in the alkyl moieties, e.g., methoxymethyl, ethoxyethyl, and the like). The peri substituents, if present, are located on carbon atoms within the heterocyclic ring or ring system which are "adjacent to" the carbon to which the ester, thiolester or amide linkage is attached. Moieties can include more than one peri substituent. For example, peri substituents can be placed in the following positions of the indicated fused ring structures:

(a) in acridiniums and acridans: on $C_1$ and $C_8$;

(b) in phenanthridiniums and reduced phenanthridiniums: on $C_7$; and (c) in quinoliniums and reduced quinoliniums: on $C_3$.

Covalently coupling the chemiluminescent label to a substrate may also be effected through reaction of functional groups contained in $R_1$, $R_2$ or $R_3$ that are the complementary to the functional group(s) present in the substrate, e.g., the specific binding material. In most cases, coupling will occur as a result of a nucleophilic reaction between the chemiluminescent label and the substrate resulting in chemical linkage of the chemiluminescent label to the substrate. The choice chemical linkage is typically the result of the reaction of an organofunctional group on the substrate that contains an active hydrogen with a complementary functional group present in the chemiluminescent label compound that reacts with the active hydrogen containing group. Illustrative of such functional groups reactive with the active hydrogen containing group includes the following:

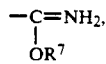

where $R^7$ is a residue of an alcohol

—N=C=S        —SO$_2$-halogen

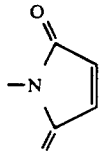 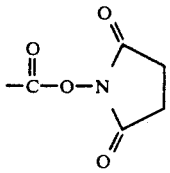 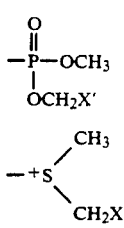

-continued

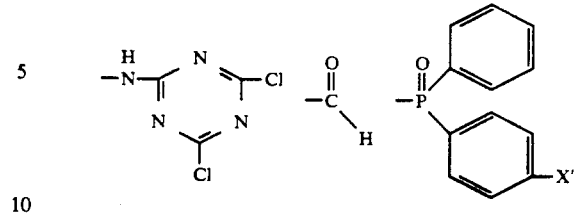

—$N_3$ and other photolabile functionalities in which halogen may be fluorine, chlorine, bromine and iodine, chlorine being the most preferred, and X' is a functional group reactive with active hydrogen, such as carboxyl halide, sulfonyl halide, amino and other groups known to be suitable for a linking reaction to proteins, nucleic acids and small molecule analytes. In addition, the functionality may be in the form of amino, mercapto, hydroxy, bonded to alkyl and aryl moieties. In the case of $R_{2 \ and \ 3}$ groups, they may comprise aryl groups that are directly joined to the heterocyclic ring or ring system or indirectly joined by a number of units, such as oxy, sulfide, sulfoxide, sulfone, amino, alkylene, alkenylene, alkynylene, alkylamino and aminoalkyl, to illustrate a few. The following groups expand the variety of functional groups that can be included in $R_{2 \ and \ 3}$ groups:

—$CO_2R^6$, where $R^6$ is hydrogen, alkyl or aryl

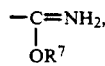

where $R^7$ is a residue of an alcohol
—$SO_2Cl$
—NCS

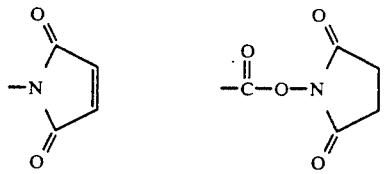

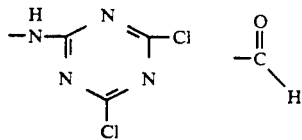

$-\overset{+}{N}(CH_3)_2(CH_2)_mCl$, where m is equal to or greater than 1

—$N_3$ and other photolabile functionalities
—$NH_2$ or oniums (such as quaternary ammoniums, phosphoniums, sulfoniums, and the like), sugars, polyalkylenepolyamines and polyalkyleneoxide (e.g., polyoxyethylene, polyoxy-1,2-propylene, polyoxy-1,3-propylene, polyoxy-1,2-butylene, etc.), and the like. Other chains, groups and functionalities useful for attaching compounds of the present invention via $R_{1, 2, 3 \ or \ 9}$ group reactions to protein are discussed in Ji, "Bifunctional Reagents," Meth. Enzymology 91:580 (1983), which is incorporated herein by reference. Methods of joining such attaching groups to protein and other materials utilize both covalent bonding and weaker chemical forces, and are well known in the art.

In addition, $R_1$, $R_2$, and $R_3$ may be organo groups that provide a number of advantages, such as operating as surface active components in compatibilizing the label compound or its conjugate in aqueous medium or to antigen structures. For example, they may comprise —$(CH_2CH_2O)_nY$, where n=1-10, and Y can be hydrogen, alkyl, and the like.

The label compounds of formula AB, including formulae A and B, comprise a heterocyclic ring (d) or ring system (c), (d) and (e) to which the ester, thiolester or amide linkage —CO—A— is attached at a carbon atom within the heterocyclic ring or ring system. That carbon atom (1) is either $sp^2$ or $sp^3$ hybridized, as shown in the two formulas, and (2) is susceptible to attack by peroxide or molecular oxygen to form the intermediate that decays to produce chemiluminescence. The oxidation state of the heteroatom within the heterocyclic ring or ring system will determine whether the carbon atom is susceptible to such attack. If the carbon to which the linkage is attached is $sp^2$ hybridized, the heteroatom is in a positive oxidation state (i.e., have a positive charge, for example, as obtained by N-alkylation or N-oxidation). If the carbon to which the linkage is attached is $sp^3$ hybridized, the heteroatom is in a neutral oxidation state (i.e., uncharged). When the heteroatom is nitrogen, proper oxidation states can be achieved only if the nitrogen is substituted with an alkyl group (including a reactive functionalized alkyl group), an aryl group (including a reactive functionalized aryl group), —O— (if the nitrogen is in a positive oxidation state) or —OH (if the nitrogen is in a neutral oxidation state). When the heteroatom is in these "proper" oxidation states, the carbon atom will be susceptible to attack by peroxide or molecular oxygen to produce the chemiluminescent intermediate.

Heterocyclic rings or ring systems that contain the heteroatom in a positive oxidation state include without limitation the following fused ring systems: acridinium, benz[a]acridinium, benz[b]acridinium, benz[c]acridinium, a benzimidazole cation, quinolinium, isoquinolinium, quinolizinium, a cyclic substituted quinolinium, phenanthridinium, and quinoxalinium. Rings or ring systems in which the heteroatom is in a neutral oxidation state include the reduced forms of the foregoing. These rings or ring systems are derived from the following rings or ring systems:

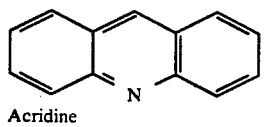
Acridine

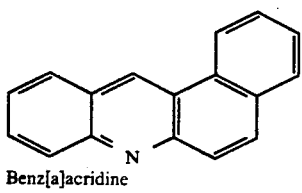
Benz[a]acridine

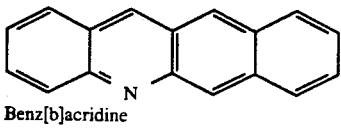
Benz[b]acridine

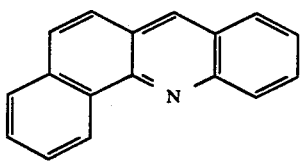
Benz[c]acridine

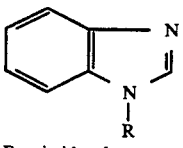
Benzimidazole

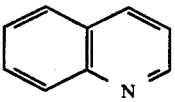
Quinoline

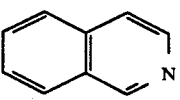
Isoquinoline

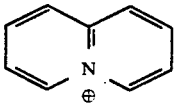
Quinolixinium Cations

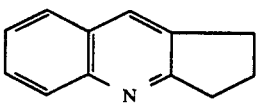

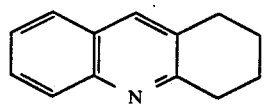

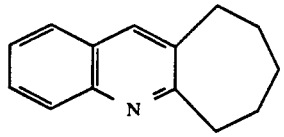
Cyclic C3, C4, C5-Substituted Quinolines

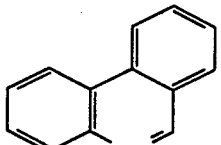
Phenanthridine

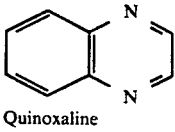
Quinoxaline

The aryl ring or ring system, represented by

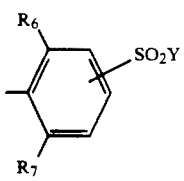

includes at least one substituted six-member ring of the formula

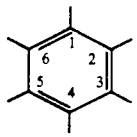

in which the substituents comprise a $SO_2Y$ at ring carbons 3, 4 or 5. The ester, amide or thiolester linkage is directly attached through a covalent bond to such six-member ring at ring carbon 1. The ring may include but is not limited to phenyl, naphthyl and anthracyl, which are derivatives of the following structures:

Phenylene

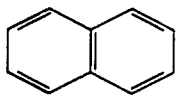

Naphthalene

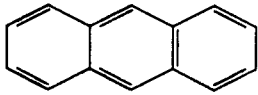

Anthracene

In those cases where naphthyl or anthracyl rings are employed, one of the rings constitutes the phenyl shown and the other ring or rings are formed in combination with any adjacent set of ring carbons thereof other than carbon 1.

$R_6$ and $R_7$ are the classic bulky electron donating groups which are located on aryl group at $C_2$ and $C_6$ so as to sterically hinder, in the traditional manner, the hydrolysis of the linkage between aryl group and the heterocyclic ring or ring system. Where the aryl is phenyl with an ester linkage being attached at position 1, $R_6$ and $R_7$ are located at the ortho 2 and 6 positions. $R_6$ and $R_7$ may be the same or different, and either may include, when they are not hydrogen:

an alkyl (such as $C_{1-4}$) or functionalized alkyl group
an aryl or functionalized aryl group
—OR, where R is alkyl (such as $C_{1-4}$) or aryl
—SR, where R is alkyl (such as $C_{1-4}$) or aryl.

The required steric hindrance can also be provided by other rings within a multi-ring unit "adjacent" to the six-member ring to which the A group is attached. In such cases, the adjacent ring is considered, in the classic sense of steric hindrance, to be an electron donating substituent which sterically hinders the hydrolysis of the linkage.

The novel esters, thiolesters and amides of the invention are produced by conventional procedures in the art. For an example, a heterocyclic acyl chloride of the formula

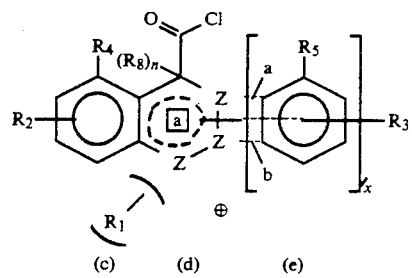

may be reacted with an 1-hydroxy, 1-mercapto, 1-amino benzene (or naphthalene or anthracene) or N-phenyl (or naphthalene or anthracene) organosulfonamide (NT) containing the desired diortho (2,6) substitution, such as those of the formula

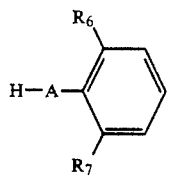

to form the desired linkage. Halosulfonation, particularly chlorosulfonation, will introduce the chlorosulfonyl groups. Chlorination of sulfonic acid groups in the product can be effected by reaction with a chlorinating agent such as thionyl chloride.

In many cases, the reactions will proceed to the formation of intermediates that require separation for the next reaction step or final products that require isolation. In such cases, conventional techniques such as distillation, extraction, crystallization, washing and the like, will be required. Conventional separation by the addition of non-solvent to a solvent solution to force precipitation of a desired material is frequently found useful.

The above-described improved chemiluminescent compounds are useful in a broad range of specific binding assays for the presence of analyte in a sample. "Presence" shall mean herein the qualitative and/or quantitative detection of an analyte. Such assays may be directed at any analyte which may be detected by use of the improved chemiluminescent compound in conjunction with specific binding reactions to form a moiety thereon. These assays include, without limitation, immunoassays, protein binding assays and nucleic acid hybridization assays.

In a typical immunoassay, the analyte is immunoreactive and its presence in a sample may be determined by virtue of its immunoreaction with an assay reagent. In a typical protein binding assay, the presence of analyte in a sample is determined by the specific binding reactivity of the analyte with an assay reagent where the reactivity is other than immunoreactivity. Examples of this include enzyme-substrate recognition and the binding affinity of avidin for biotin. In the typical nucleic acid hybridization assay, the presence of analyte in a sample is determined by a hybridization reaction of the analyte with an assay reagent. Analyte nucleic acid (usually present as double stranded DNA or RNA) is usually first converted to a single stranded form and immobilized onto a carrier (e.g., nitrocellulose paper). The analyte nucleic acid may alternatively be electrophoresed into a gel matrix. The immobilized analyte may then be hybridized (i.e., specifically bound) by a complementary sequence of nucleic acid.

The foregoing specific binding assays may be performed in a wide variety of assay formats. These assay formats fall within two broad categories. In the first category, the assay utilizes a chemiluminescent conjugate which comprises the improved chemiluminescent moiety attached to a specific binding material. "Specific binding material" means herein any material which will bind specifically by an immunoreaction, protein binding reaction, nucleic acid hybridization reaction, and any other reaction in which the material reacts specifically with a restricted class of biological, biochemical or chemical species. In this category of assays, the chemiluminescent conjugate participates in a specific binding reaction and the presence of analyte in the sample is proportional to the formation of one or more specific binding reaction products containing the chemiluminescent conjugate. The assay is performed by allowing the requisite specific binding reactions to occur under suitable reaction conditions. The formation of specific binding reaction products containing the chemiluminescent conjugate is determined by measuring the chemiluminescence of such products containing the chemiluminescent conjugate or by measuring the chemiluminescence of unreacted or partially reacted chemiluminescent conjugate not contained in such products.

This first category of assay formats is illustrated by sandwich assays, competitive assays, surface antigen assays, sequential saturation assays, competitive displacement assays and quenching assays.

In a sandwich format, the specific binding material to which the chemiluminescent moiety is attached, is capable of specifically binding with the analyte. The assay further utilizes a reactant which is capable of specifically binding with the analyte to form a reactant-analyte-chemiluminescent conjugate complex. The reactant may be attached to a solid phase, including without limitation, dip sticks, beads, tubes, paper or polymer sheets. In such cases, the presence of analyte in a sample will be proportional to the chemiluminescence of the solid phase after the specific binding reactions are completed. Such assay formats are discussed further in U.S. Pat. Nos. 4,652,533, 4,383,031, 4,380,580 and 4,226,993, which are incorporated herein by reference.

In a competitive format, the assay utilizes a reactant which is capable of specifically binding with the analyte to form an analyte-reactant complex and with the specific binding material, to which the chemiluminescent moiety is attached, to form a chemiluminescent conjugate-reactant complex. The reactant may be attached to a solid phase, or alternatively reaction products containing the reactant may be precipitated by use of a second antibody or by other known means. In this competitive format, the presence of analyte is "proportional," i.e., inversely proportional, to the chemiluminescence of the solid phase or precipitate. A further discussion of this assay format may be found in the immediately above mentioned U.S. patents.

In another assay format, the analyte may occur on or be bound to a larger biological, biochemical or chemical species. This type of format is illustrated by a surface antigen assay. In this format, the specific binding material is capable of specifically binding with the analyte and the presence of analyte is proportional to the analyte-chemiluminescent conjugate complex formed as a reaction product. This is illustrated by attaching the chemiluminescent moiety to an antibody which is specific to a surface antigen on a cell. The presence of the cell surface antigen will be indicated by the chemiluminescence of the cells after the completion of the reaction. The cells themselves may be used in conjunction with a filtration system to separate the analyte-chemiluminescent conjugate complex which is formed on the surface of the cell from unreacted chemiluminescent conjugate. This is discussed further in U.S. Pat. No. 4,652,533.

The improved chemiluminescent moiety may be used in additional assay formats known in the art including without limitation sequential saturation and competitive displacement, both of which utilize a chemiluminescent conjugate where both (1) the specific binding material, to which the moiety is attached, and (2) the analyte specifically bind with a reactant. In the case of sequential saturation, the analyte is reacted with the reactant first, followed by a reaction of the chemiluminescent conjugate with remaining unreacted reactant. In the case of competitive displacement, the chemiluminescent conjugate competitively displaces analyte which has already bound to the reactant.

In a quenching format, the assay utilizes a reactant which is capable of specifically binding with the analyte to form an analyte-reactant complex and with the specific binding material, to which the chemiluminescent moiety is attached, to form a chemiluminescent conjugate-reactant complex. A quenching moiety is attached to the reactant. When brought into close proximity to the chemiluminescent moiety, the quenching moiety reduces or quenches the chemiluminescence of the chemiluminescent moiety. In this quenching format, the presence of analyte is proportional to the chemiluminescence of the chemiluminescent moiety. A further discussion of this format may be found in U.S. Pat. Nos. 4,220,450 and 4,277,437, which are incorporated herein by reference.

In consideration of the above discussed assay formats, and in the formats to be discussed below, the order in which assay reagents are added and reacted may vary widely as is well known in the art. For example, in a sandwich assay, the reactant bound to a solid phase may be reacted with an analyte contained in a sample and after this reaction the solid phase containing complexed analyte may be separated from the remaining sample. After this separation step, the chemiluminescent conjugate may be reacted with the complex on the solid phase. Alternatively, the solid phase, sample and chemiluminescent conjugate may be added together simultaneously and reacted prior to separation. As a still further but less preferred alternative, the analyte in the sample and the chemiluminescent conjugate may be reacted prior to addition of the reactant on the solid phase. Similar variations in the mixing and reaction steps are possible for competitive assay formats as well as other formats known in the art. "Allowing under suitable conditions substantial formation" of specific binding reaction products shall herein include the many different variations on the order of addition and reaction of assay reagents.

In the second category of assay formats, the assay utilizes an unconjugated improved chemiluminescent compound. The presence of analyte in the sample is proportional to the formation of one or more specific binding reaction products which do not themselves contain the chemiluminescent moiety. Instead, the chemiluminescent compound chemiluminesces in proportion to the formation of such reaction products.

In one example of this second category of assays, the assay utilizes a reactant capable of binding with the analyte to form an analyte-reactant complex which causes the chemiluminescent compound to chemiluminesce. This is illustrated by a simple enzyme-substrate assay in which the analyte is the substrate glucose and the reactant is the enzyme glucose oxidase. Formation of the enzyme-substrate complex triggers the chemiluminescent compound. Such enzyme-substrate assay for glucose is disclosed in U.S. Pat. Nos. 3,964,870 and 4,427,770, both of which are incorporated herein by reference. This enzyme-substrate assay is a specific binding assay in the sense that the substrate specifically binds to the active site of the enzyme in much the same way that an antigen binds to an antibody. In this assay, the enzyme specifically binds with the substrate which results in the production of peroxide which, in turn, causes the chemiluminescent compound to chemiluminesce.

Also included in the second category of assays are those assays in which the formation of the reaction products promotes or inhibits chemiluminescence by the chemiluminescent compound in a less direct manner. In this assay, a first reactant, which is cross reactive with the analyte, is attached to an enzyme such as glucose oxidase close to its active site. A second reactant which is specific for both the analyte and the immunoreactive material is added to the sample and the altered enzyme in the presence of the substrate (i.e., glucose). When the second reactant binds to the first reactant located near the active site on the enzyme, the second reactant blocks the active site in a way that the substrate cannot bind to the enzyme at the active site or the binding of the substrate at the active site is significantly decreased. The second reactant blocking the enzyme in this manner inhibits the enzyme from producing peroxide which, in turn, would have triggered the chemiluminescent moiety. Analyte in the sample, however, will tie up the second reactant, thus preventing the second reactant from inhibiting the production of peroxide. The presence of analyte will be proportional to the chemiluminescence of the compound.

The assays contained in the above two categories of assay formats may be heterogeneous or homogeneous. In heterogeneous assays, the reaction products, whose formation is proportional to the presence of analyte in the sample, are separated from other products of the reaction. Separation can be achieved by any means, including without limitation, separation of a liquid phase from a solid phase by filtration, microfiltration, double antibody precipitation, centrifugation, size exclusion chromatography, removal of a solid phase (e.g., a dip stick) from a sample solution or electrophoresis. For example, in a sandwich assay the reactant-analyte-chemiluminescent conjugate complex is separated from unreacted chemiluminescent conjugate. In a surface antigen assay, the analyte-chemiluminescent conjugate complex is separated from unreacted chemiluminescent conjugate. In a competitive assay, the reactant-chemiluminescent conjugate complex is separated from unreacted chemiluminescent conjugate. In a sequential saturation assay and in a competitive displacement assay, the reactant-chemiluminescent conjugate complex is separated from unreacted chemiluminescent conjugate. Alternatively, in homogeneous assays the reaction products are not separated. After the assay reagents have been allowed to react, the chemiluminescence may be measured from the whole assay mixture whether such mixture is in solution, on a solid phase or distributed between various membrane layers of a dip stick or other solid support. The glucose assay using glucose oxidase and a chemiluminescent moiety illustrates a simple homogeneous assay in which separation is unnecessary. The quenching assay illustrates a more complex homogeneous assay in which separation is unnecessary. It is contemplated that either category of assay formats may give rise to either heterogeneous or homogeneous formats.

Finally, "measuring the chemiluminescence" shall include, where relevant, the act of separating those specific binding reaction products, the formation of which are proportional to the presence of analyte in the sample, from other reaction products. It shall also include, where relevant, the acts of triggering the chemiluminescent moiety to chemiluminesce in the case of those assay formats in which the formation of the reaction products does not itself trigger the chemiluminescent moiety.

SYNTHESIS OF MOIETIES

The following examples show the synthesis of certain chemiluminescent moieties of the present invention. These chemiluminescent moieties are typically made in small quantities and the procedures employed for their manufacture do not reflect conventional large scale chemical manufacturing procedures. In these reactions, conventional reactions have been employed to produce the chemiluminescent labels of the invention. Purification procedures suitable for isolating product are conventional laboratory procedures, such as crystallization out of solvent solution by the addition of a nonsolvent, solvent extraction, and the like. In such cases, many different solvents and nonsolvents are suitable. Yields are the amounts recovered as a percentage of reactants employed.

EXAMPLE 1

A chemiluminescent label the present invention is (2,6-dimethoxy-3-chlorosulfonyl) phenyl-N-methyl-acridinium-9-carboxylate fluorosulfonate which has the following formula:

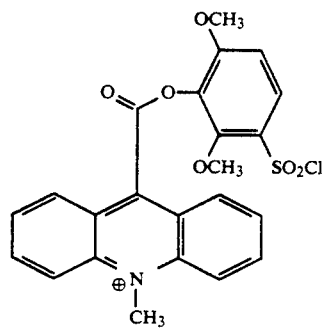

This compound (2,6-dimethoxy-3-chlorosulfonyl)phenyl-N-methyl-acridinium-9-carboxylate fluorosulfonate, was synthesized according to the following scheme:

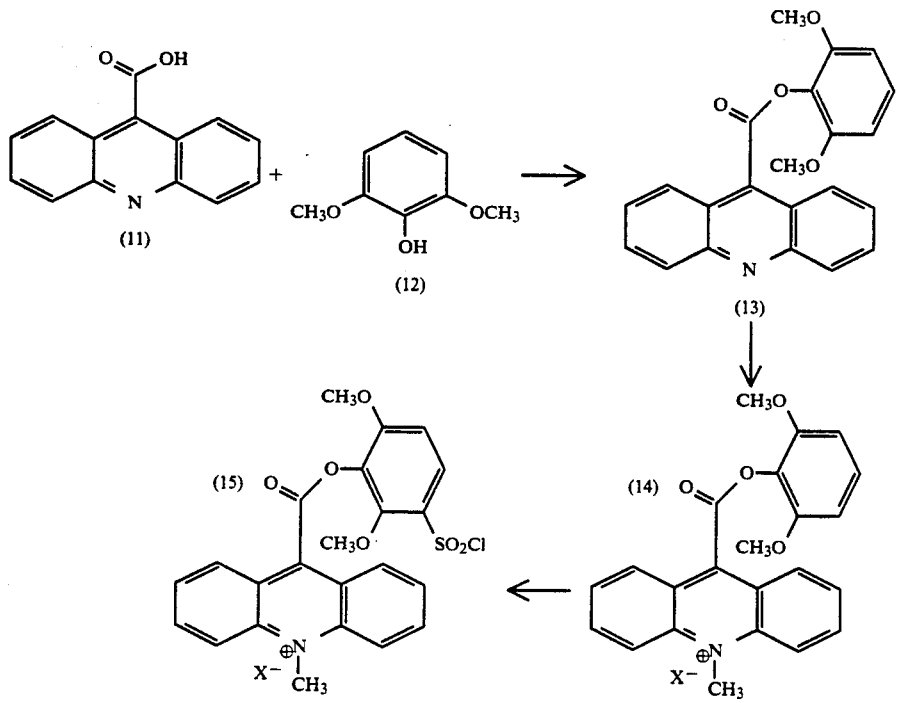

Esterification of acridine-9-carboxylic acid (11) with 2,6-dimethoxyphenol (12) via the acid chloride (not shown) provides the ester (13). Methylation of the acridine nitrogen with methylfluorosulfate (14) and subsequent chlorosulfonation with chlorosulfonic acid gives the label (15). These reactions are described in further detail in the following.

Acridine-9-carboxylic acid (11) (6.10 g, 0.027 moles) in a 250 ml round bottom flask was mixed with thionyl chloride (130 ml) and the mixture was refluxed for 2 hours with stirring. The excess thionyl chloride was removed in a rotary evaporator. The residue was treated with benzene (75 ml) and the solvent was removed in vacuo to remove traces of thionyl chloride. The residue of acridine-9-carbonyl chloride (11) was mixed with pyridine (130 ml) and 2,6-dimethoxyphenol (12) (4.16 g, 0.027 moles) was added. The mixture was warmed using a water bath (about 60° C.) to dissolve all the solids. After 15 hours of stirring at room temperature the mixture was poured into 1 liter of water. The suspension was acidified with concentrated hydrochloric acid to pH 2.0. The solid product was filtered, washed with water and dissolved in chloroform. Drying (anhydrous sodium sulfate) and evaporation of chloroform gave (2,6-dimethoxy)phenyl-acridine-9-carboxylate (13). This was chromatographed on a silica gel column using CHCl$_3$/EtOAc, 98:2 as solvent. The fractions with R$_f$ value of 0.19 on TLC with the same solvent were pooled and evaporation of the solvents gave the pure ester (13) (yield=30%). Esterification may also be effected with the procedure of Brewster et al., *J. Am. Chem. Soc.*, 77, 6214-6215 (1955).

The compound (2,6-dimethoxy)phenyl-acridine-9-carboxylate (13) (2.01 g, 5.6 mmole) was dissolved in dichloromethane (110 ml, anhydrous) in a 250 ml round bottom flask. Methyl fluorosulfate (4.60 ml, 6.48 g, 56 mmoles) was added and the mixture was stirred at room temperature for 15 hours. Anhydrous ether (100 ml) was added and the precipitated bright yellow solids were filtered after stirring the suspension for 0.5 hours. The solid was washed well with ether (about 100 ml) and then with pentane (50 ml). The acridinium was recrystallized from acetonitrile to provide pure 2,6-dimethoxy-phenyl-acridinium-9-carboxylate fluorosulfonate (14) (yield=81%). The same results may be achieved by crystallization from acetonitrile by the addition of ethyl acetate. Other useful solvent combinations include alcohol and ether, such as methanol, ethanol or propanol and diethyl ether (ether is the precipitating solvent).

In a dry two neck 25 ml round bottom flask were placed the (2,6-dimethoxy)phenyl-10-methyl acridinium-9-carboxylate fluoro-sulfonate (14) (101.7 mg, 0.215 mmole), a magnetic stirring bar and anhydrous CH$_2$Cl$_2$ (5 ml). The suspension was stirred and cooled to −20° C. in a CCl$_4$/dry ice bath. Chlorosulfonic acid (72 µl, 0.125 g, 1.07 mmole) was added and stirring continued at −20° C. for 30 minutes. The reaction mixture was then allowed to warm slowly to room temperature and stirred for an additional 2 hours. Anhydrous ether (5 ml) was added to the reaction flask causing the formation of a light yellow precipitate. It was filtered and washed thoroughly with ether. Drying under vacuum gave (2,6-dimethoxy-3-chlorosulfonyl)phenyl acridinium-9-carboxylate fluorosulfonate (15) (yield=94.3%). MS: FAB, dithiothreitol/dithioerythrytol matrix, 472 (M+).

A modification of this procedure, the chlorosulfonyl content of the compound (15) can be increased (see March, *Advanced Organic Chemistry*, John Wiley & Sons, p. 445 (1985)) by single or multiple treatments with thionyl chloride, phosphorus pentachloride, and the like. The chlorosulfonyl content of the compound is not critical to its use as a label so long as the stoichiometry for appropriate conjugation of chlorosulfonyl to the complementary group on the specific binding material, viz., lysine amino group, is achieved. The resulting conjugate is desirably purified. It is preferred to have a chlorosulfonyl content of at least 30 weight percent of the weight of the composition.

EXAMPLE 2

Another chemiluminescent label of the present invention is (2,6-dimethyl-3-chlorosulfonyl)phenyl-N-methyl-acridinium-9-carboxylate fluorosulfonate which has the following formula:

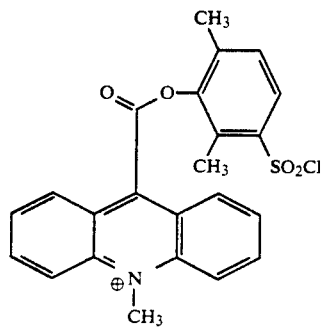

boxylate fluorosulfonate with the substitution of 2,6-dimethylphenol for 2,6-dimethoxyphenol in the esterification step.

EXAMPLE 3

The compound (2,6-dimethoxy-3-chlorosulfonyl-phenyl)-2-phenyl-N-methyl-quinolinium-4-carboxylate fluorosulfonate, which has the following formula:

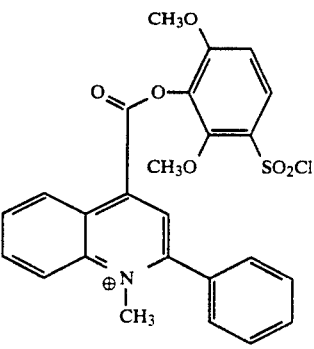

is synthesizable according to the following scheme:

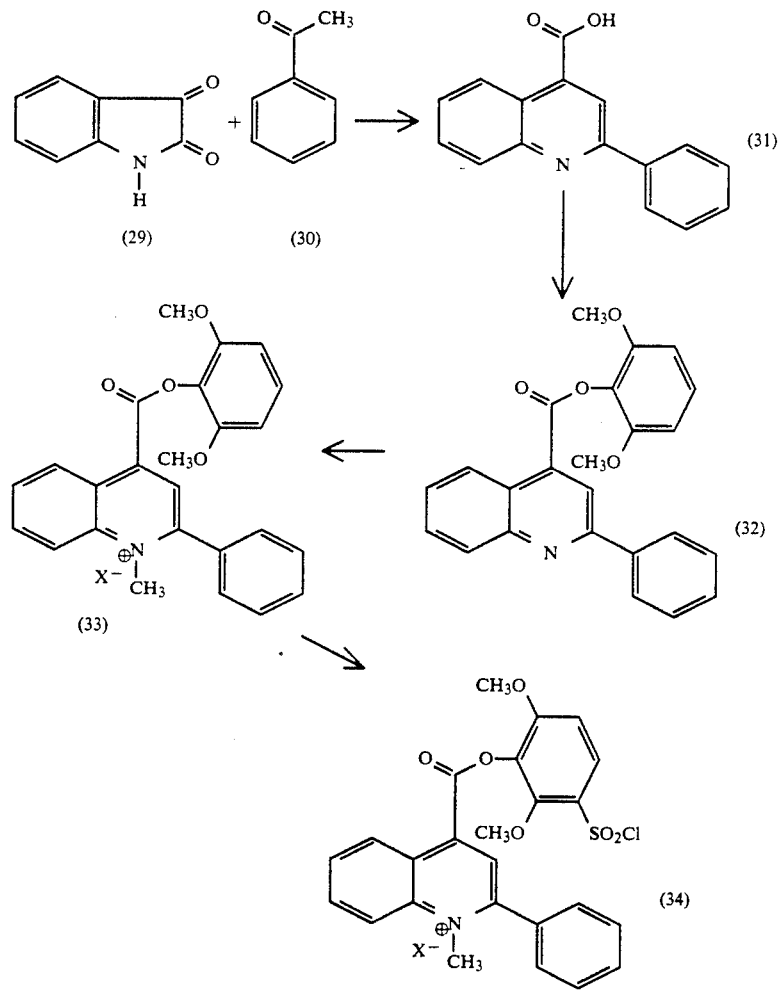

The compound (2,6-dimethyl-3-chlorosulfonyl)phenyl-N-methyl-acridinium-9-carboxylate fluorosulfonate was synthesized by the same method as (2,6-dimethoxy-3-chlorosulfonyl)phenyl-N-methyl-acridinium-9-car- Acetophenone (29) (120 g, 1 mol) and isatin (30) (147 g, 1 mol) would be refluxed for 10 hours in water and ethanol, with potassium hydroxide (17 g). The 2-phenyl-quinoline-4-carboxylic acid (31) is recovered from ethanol as white needles.

The 2-phenyl-quinoline carboxylic acid (31) (735 mg, 3 mmoles) is dissolved in anhydrous pyridine (14 ml) and cooled in an icewater bath. Para-toluene sulfonyl chloride (1.15 g, 6 mmoles) is added and the mixture stirred for 15 mins. Then 2,6-dimethoxy phenol (462 mg, 3 mmoles) is added and the mixture stirred at room temperature for 15 hours. The solution is poured into ice water (300 ml) and the (2,6-dimethoxy)phenyl-2-phenyl-quinoline-4-carboxylate (32) would be filtered. The solids are dried and purified on a silica gel column using chloroform/hexane (1:1).

Methyl fluorosulfate (492 μl, 0.69 g, 6 mmoles) is added to the ester (32) (381 g, 1 mmole) dissolved in anhydrous methylene chloride (3 ml). After stirring for 15 hours at room temperature under nitrogen, anhydrous ether (20 ml) is added. The (2,6-dimethoxy)phenyl-2-phenyl-quinoline-4-carboxylate-N-methylate (33) is filtered and washed with ether and dried.

The ester (33) (200 mg, 0.4 mmole) was suspended in anhydrous methylene chloride (5 ml) and cooled in a dry ice/CCl$_4$ bath under nitrogen in a dry two neck 25 ml round bottom flask. Chlorosulfonic acid (144 μl, 2 mmole) is added and stirring continued at $-20°$ C. for 0.5 hours. The mixture is then allowed to warm slowly to room temperature and stirred for an additional 2 hours. Anhydrous ether (20 ml) is added and the precipitated (2,6-dimethoxy-3-chlorosulfonyl)phenyl-2-phenyl-N-methyl-quinolinium-4-carboxylate fluorosulfonate (34) filtered and washed with ether and dried.

EXAMPLE 4

A solution of 2,6-dimethyl-3-chlorosulfonyl phenyl acridinium-9-carboxylate fluorosulfonate (0.355 mg.) in a mixture of 188 μl acetonitrile and 100 μl DMF was placed in a 2 ml clear screw-capped vial. A solution of glycine benzyl ester p-toluene sulfonate salt (2.63 mg) in 150 μl acetonitrile containing 0.71 μl triethylamine was prepared. The two solutions were mixed and left standing for 1 hour and 15 minutes at room temperature (about 23° C.). The reaction product was isolated and purified on an HPLC system using a C$_{18}$ reverse phase column and acetonitrile:water (0.1% trifluoroacetic acid) in a ratio of 60/40 as the mobile phase. The isolated product had the formula:

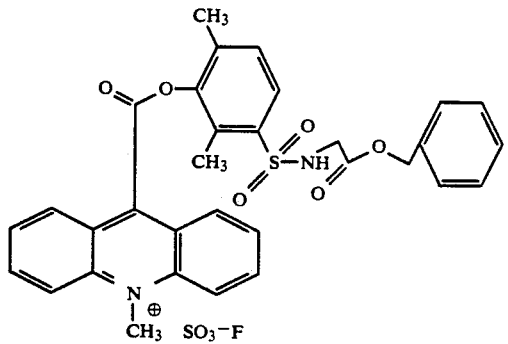

EXAMPLE 5

The following procedure for attaching to protein is generally applicable to chemiluminescent labels of the present invention.

Mouse IgG (Sigma, 1 mg) was dissolved in 0.9 ml phosphate buffer (100 mM, pH 8.0, 150 mM). If desired, higher pH may be employed, such as a pH as high as 9.5. The solution was then divided into three equal portions of 0.33 mg/0.3 ml (0.0022 μmoles). About 0.3 mg of a moiety of the present invention was dissolved in about 0.4 ml DMF so as to obtain 0.022 moles of moiety in 15 μl DMF.

0.022 μmoles of the compound of the present invention was mixed with 0.0022 μmoles of IgG in a plastic microcentrifuge tube. After 15 minutes, an additional 0.022 μmoles of compound was added to the microcentrifuge tube (compound to protein molar ratio was 20:1). After an additional 15 minutes, excess amounts of the compound of the present invention were quenched with lysine HCl solution (10 μl in 100 mM pi buffer, pH 8.0) for 15 minutes.

Alternatively, aliquots of 0.0055 μmoles of the compound of the present invention was used instead of 0.022 μmoles (compound to protein molar ratio was 5:1).

Biorad glass columns (1 cm×50 cm) (commercially available from Biorad, Chemical Division, Richmond, Calif.) were packed with previously swelled and deaerated Sephadex G-50-80 in phosphate buffer (100 mM, pH 6.3, 150 mM NaCl, 0.001% Thimerosal) to a bed volume of 45 ml. The reaction solution was run through the columns at a flow rate of 0.3–0.4 ml/min. 0.5 ml fractions were collected. Labelled protein fractions were detected by diluting 20 μl from each fraction to 1 ml and determining the chemiluminescence produced with 30 μl of the diluted solution. Labelled fractions were then pooled.

The pooled conjugate fractions were dialyzed to improve the purity of immunoreactive conjugate. The pooled fractions were dialyzed against 500 ml pH 6.3 phosphate buffer (100 mM, pH 6.3, 150 mM NaCl, 0.001% TMS) over a period of 24 hours with three buffer changes.

General labeling procedure for sulfonyl chloride based acridinium esters.

Anti-TSH antibody (1 mg) is transferred to a Centricon 30 (ultrafiltration unit, Amicon, Beverly, Mass.) and 1 ml bicarbonate buffer (15 mM, pH 9.6) is added. The buffer is centrifuged and the volume of solution brought up to 400 μl using the same buffer. A solution of the compound of Example 4 of the formula

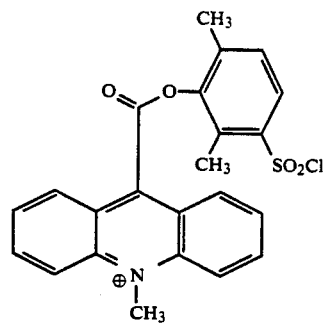

in DMF (N,N-dimethylformamide, 2 mg/mL, 21.6 μl) is added to the anti-TSH antibody and the Centricon is gently mixed for 15 minutes by hand. Another 21.6 μl from a freshly made DMF solution of the same compound, is added at the end of 15 minutes. A total of 24 moles of the compound to antibody, is used in the reaction. Fifteen minutes from the second addition, the protein solution is purified from the unreacted compound using a Sephadex desalting column (Pharmacia HR-10/10), an HPLC system, and a eluent solvent comprising 1 part ethanol and 4 parts phosphate buffer (100 mM sodium phosphate, 300 mM sodium chloride, pH 6.0). The protein fraction is collected and the eluent solvent is exchanged with phosphate buffer (pH 6.3) in a Centricon 30. The concentrate acridinium labelled anti-TSH antibody is diluted into 25 ml of diluent buffer (sodium phosphate buffer 100 mM, sodium chloride 150 mM, Thimerosal 0.001%, 0.4% BSA, 0.1 mg/ml each (0.001%) of mouse and goat γ-globulins, pH 6) after filtration through a 0.45 micron syringe filter. The diluted 25 milliliters is stored at −20° C. as a stock solution to make TSH labelled antibody reagent after appropriate dilutions.

ASSAY PROTOCOLS

EXAMPLE 6

1. Components

A) Labelled Antibody (conjugate): Affinity purified rabbit antiprolactin conjugated to (2,6-dimethoxy-3-chlorosulfonyl)phenyl-N-methyl-acridinium-9-carboxylate fluorosulfonate. Storage buffer: 10 mM phosphate buffer, 100 mM NaCl pH 6.0, 0.001% Thimerosal, 0.4% BSA.

B) Capture antibody: Rabbit anti-prolactin (6 µg/ml) as a solid phase on Nunc ® tubes (commercially available from Midland Scientific, Roseville, Minn.).

C) Solid-phase coated tubes: Dried Nunc ® tubes were prepared as follows:
 1) 0.3 ml of the capture antibody per tube at 6 µg/ml in PBS buffer (phosphate buffer saline, pH 7.2–7.4, 10 mM phosphate, 100 mM NaCl, 10 mM NaN$_3$) was pipetted into Nunc ® tubes.
 2) Tubes were incubated for 18–24 hours.
 3) Tubes were washed 2 times with the PBS buffer.
 4) Tubes were blocked with 2.0% BSA in PBS buffer. Incubate for <4 hours at room temperature.
 5) Tubes were washed 3 times with PBS buffer.
 6) Tubes were dried at room temperature.
 7) Tubes were stored in plastic freezer bags at 4° C.

D) Standards: Prepared in horse serum 0, 5, 30, 100 and 200 ng/ml.

2. Assay Protocol 1) 25 µl of sample or standard was pipetted into the antibody-coated tubes. 2) 100 µl of labelled antibody was added. 3) Tubes were vortexed gently. 4) Tubes were incubated for 1 hour at room temperature on a rotator. 5) Tubes were washed 3 times with deionized water. 6) Chemiluminescence was counted for 2 seconds [pump 1: 0.1 N HNO$_3$+0.25% H$_2$O$_2$; pump 2:0.25 N NaOH+0.125% CTAC] in a LumaTag TM Analyzer (commercially available from London Diagnostics, Eden Prairie, Minn.).

EXAMPLE 7

1. Components

A) Progesterone Conjugate of a b-D-thioglucose adduct of (2,6-dimethoxy-3-chlorosulfonyl)phenyl-N-methyl-acridinium-9-carboxylate fluorosulfonate: 20 pg/ml progesterone conjugate in phosphate buffer (pH 6.0, 100 mM phosphate, 150 mM NaCl, 0.1% human serum albumin, 0.001% Thimerosal).

B) Primary antibody: Rabbit anti-progesterone (Cambridge Medical Diagnostics) in phosphate buffer (pH 6.0, 200 mM phosphate, 150 mM NaCl, 0.1% human serum albumin, 0.01% CHAPS, 5 µg Danazol).

C) Solid-phase coated tubes: Dried Nunc ® tubes coated with 2.5 µg of Goat anti-Rabbit fc and blocked with 0.5% BSA. Tubes were prepared as follows:
 1) Tubes were incubated for 1 hour with 2.5 µg/ml Goat anti-Rabbit fc (500 µl) at room temperature.
 2) Tubes were washed 3 times with distilled water.
 3) Tubes were immediately incubated for 3 hours with 0.5% BSA (500 µl) at room temperature.
 4) Tubes were washed 3 times with distilled water.
 5) Tubes were dried overnight at 40% relative humidity at room temperature.
 6) Tubes were stored in plastic freezer bags at 4° C.

D) Serum matrix: Antech steer serum.

E) Standards: 0, 0.13, 0.38, 1.31, 7.31 16.6 and 37.0 ng/ml.

2. Assay Protocol 1) 50 µl of sample or standard was pipetted into the antibody-coated tubes.
2) 100 µl of conjugated buffer was added.
3) 100 µl of primary antibody buffer was added.
4) Tubes were vortexed gently.
5) Tubes were incubated for 2 hours at 37° C.
6) Tubes were decanted and washed with 150 mM NaCl in 0.1% Tween (1 ml) and then 3 times with distilled water.
7) Tubes were inverted and allowed to drain.
8) Chemiluminescence was counted for 2 seconds[pump 1: 0.1N HNO$_3$+0.25% H$_2$O$_2$; pump 2: 0.25N NaOH+0.125% CTAC] in a LumaTag TM Analyzer (commercially available from London Diagnostics, Eden Prairie, Minn.).

EXAMPLE 8

1. Components

A) Labelled Ab: Affinity purified goat anti-TSH conjugated to (2,6-dimethoxy-3-chlorosulfonyl)phenyl-N-methyl-acridinium-9-carboxylate fluorosulfonate.

B) Storage buffer: 100 mM phosphate, 0.145M NaCl, 0.001% Thimerosal, 0.4% BSA, 0.1 mg/ml mouse-globulins, and 0.1 mg/ml goat-globulins, pH 6.0.

C) Capture antibody: Monoclonal-anti-TSH (2 µg/ml) as a solid phase on Nunc ® tubes. Procedure for preparation of solid-phase Nunc ® tubes:
 1) 0.4 ml of the capture antibody at 2 µg/ml in PBS buffer (phosphate buffer saline, pH 7.2–7.4, 10 mM phosphate, 100 mM NaCl, 10 mM NaN$_3$) was added to each tube.
 2) Tubes were incubated for 18–24 hours.
 3) Tubes were washed 3 times with the PBS buffer.
 4) Tubes were block with 2.0% BSA in PBS buffer and incubated for <4 hours at room temperature.
 5) Tubes were washed 3 times with PBS buffer.
 6) Tubes were dried at room temperature.
 7) Tubes were stored in plastic freezer bags at 4° C.

D) Standards: Prepared in horse serum. 0, 0.5, 2.5, 10, 25 and 100 µIU/ml

2. Assay Protocol 1) 200 µof sample was pipettd into the coated tubes.
2) 100 µl of labelled antibody was added.
3) Tubes were vortexed gently.
4) Tubes were incubated for 2 hours at room temperature on a shaker.

5) Tubes were washed using a Biotomic washer (commercially available from Ocean Scientific, Inc., Garden Grove, Calif.).

6) Chemiluminescence was counted for 2 seconds [pump 1: 0.1N $HNO_3$+0.25% $H_2O_2$; pump 2: 0.25N NaOH+0.125% CTAC] in a LumaTag ™ Analyzer (commercially available from London Diagnostics, Eden Prairie, Minn.

From the foregoing, it will be obvious to those skilled in the art that various modifications in the above-described compositions and methods can be made without departing from the spirit and scope of the invention. Accordingly, the invention may be embodied in other specific forms without departing from the spirit or essential characteristics thereof. Present embodiments, therefore, are to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. A chemiluminescent aryl ester, thioester or amide of a carboxylic acid substituted heterocyclic ring that is susceptible to chemical attack to dissociate the heterocyclic ring to a transient compound, wherein the heterocyclic ring is ring carbon-bonded to the carbonyl of the ester, thioester or amide moiety and possesses a heteroatom in an oxidation state that allows chemiluminescence by dissociating a compound at the carbon bonded to the carbonyl that decays to produce chemiluminescence, the aryl is a ring or ring system that is ring carbon-bonded to the oxygen, sulfur or nitrogen of the ester, thioester or amide, as the case may be, and contains at least diortho substituents thereon and $-SO_2$ bonded directly by a sulfur to carbon bond at the meta or para position.

2. The chemiluminescent aryl ester, thioester or amide of a carboxylic acid substituted heterocyclic ring of claim 1 wherein the diortho substituent are electron donating.

3. A chemiluminescent labeling composition comprising an ester, thioester or amide covalently and jointly bonded to (1) a carbon of a heterocyclic ring or ring system that is susceptible to attack by peroxide or molecular oxygen and (2) an aryl ring or ring system wherein the heterocyclic ring or ring system is distinguished by a heteroatom thereof an oxidation state that causes the attacked carbon atom to chemiluminesce; the aryl ring or ring system contains at least three substituents, two of which are ortho substituents that are electron donating and at least one of which is a $-SO_2$ meta or para substituent that is bonded directly by a sulfur to aryl ring carbon bond.

4. A hydrolytically stable heterocyclic composition capable of chemiluminescent properties when labeled to a specific binding material by chemically-induced dissociation, comprising
 (a) an aryl ring,
 (b) a sterically-hindered ester, thioester or amide linkage moiety with enhanced hydrolytic stability, and
 (c) a heterocyclic organic ring moiety, in which
  (1) the carbonyl carbon of (b) is covalently bonded to a carbon atom (x) of (c) and the remaining free valence of (b) is carbon bonded to an aromatic ring carbon atom (y) of (a),
  (2) (a) contains two electron donating groups located on the ring carbon atoms adjacent to (y), the meta and/or para positions to (y) contain $-SO_2$—halide bonded directly to the ring by a sulfur to ring carbon bond, and
  (3) (c) contains a ring member heteroatom in an oxidation state that provides such chemiluminescence properties.

5. A hydrolytically stable conjugate possessing chemiluminescent properties by chemical dissociation, comprising a chemiluminescent label bonded to a specific binding material that contains
 (a) an aryl ring,
 (b) a sterically-hindered ester, thioester or amide linkage moiety with enhanced hydrolytic stability, and
 (c) a heterocyclic organic ring moiety, in which
  (1) the carbonyl carbon of (b) is covalently bonded to a carbon atom (x) of (c) and the remaining free valence of (b) is carbon bonded to an aromatic ring carbon atom (y) of (a),
  (2) (a) contains two substituent groups that are electron donating and located on the ring carbon atoms adjacent to (y), the meta and/or para positions to (y) contain $-SO_2$—halide bonded directly to the ring by a sulfur to ring carbon bond, and
  (3) (c) contains a ring member heteroatom that is in an oxidation state whereby reaction of molecular oxygen or a peroxide with said composition forms an intermediate which decays to produce chemiluminescence.

6. The chemiluminescent labeling composition of claim 1 conjugated with a specific binding material.

7. A chemiluminescent assay comprising the conjugate of claim 5.

8. A chemiluminescent assay kit comprising the conjugate of claim 6.

9. A hydrolytically stable heterocyclic composition capable of chemiluminescent properties when labeled to a specific binding material, by reaction with peroxide or molecular oxygen, comprising
 (a) an aryl ring,
 (b) a sterically-hindered ester, thioester or amide linkage moiety with enhanced hydrolytic stability, and
 (c) a heterocyclic organic ring moiety, in which
  (1) the carbonyl carbon of (b) is covalently bonded to a carbon atom (x) of (c) and the remaining free valence of (b) is carbon bonded to an aromatic ring carbon atom (y) of (a),
  (2) (a) contains diortho alkyl substituent groups hindering hydrolysis of (b) and $-SO_2Cl$ meta and/or para to (y),
  and (c) contains a ring member heteroatom in an oxidation state that
  provides such chemiluminescence properties.

10. A hydrolytically stable conjugate possessing chemiluminescent properties by reaction of molecular oxygen or a peroxide therewith, comprising a chemiluminescent label bonded to a specific binding material that contains
 (a) an aryl ring,
 (b) a sterically-hindered ester, thioester or amide linkage moiety with enhanced hydrolytic stability, and
 (c) a heterocyclic organic ring moiety, in which (1) the carbonyl carbon of (b) is covalently bonded to a carbon atom (x) of (c) and the remaining free valence of (b) is carbon bonded to an aromatic ring carbon atom (y) of (a), 2) (a) contains two substituent groups hindering hydrolysis of (b) that are located on the ring carbon atoms adjacent to (y), and a sulfonamide group, meta and/or para to (y), that is bonded to the specific binding material, and (c) contains a ring member heteroatom that is in an oxidation state whereby reaction of molecular oxygen or a peroxide with said composition forms an intermediate which decays to produce chemiluminescence.

11. An assay for the presence of an analyte in a sample comprising contacting an analyte with the chemiluminescent-labeled specific binding material of claim 10, inducing chemiluminescence by decay of an intermediate formable in the presence of peroxide or molecular oxygen, and measuring chemiluminescence therefrom to assay the analyte.

12. A specific binding assay kit comprising a vial containing a conjugate possessing chemiluminescent properties by reaction of molecular oxygen or a peroxide therewith and containing the chemiluminescent label bonded to a specific binding material of claim 10.

13. The chemiluminescent label composition of claim 1 wherein the composition is (2,6-dimethoxy-3-chlorosulfonyl)-phenyl-N-methyl-acridinium-9-carboxylate.

14. The chemiluminescent label composition of claim 1 wherein the composition is (2,6-dimethyl-3-chlorosulfonyl)-phenyl-N-methyl-acridinium-9-carboxylate.

15. A conjugate of the reaction product of a specific binding material and the chemiluminescent label composition of claim 13.

16. A conjugate of the reaction product of a specific binding material and the chemiluminescent label composition of claim 14.

17. An assay for the presence of an analyte in a sample comprising contacting an analyte with the chemiluminescent-labeled specific binding material of claim 15, inducing chemiluminescence by decay of an intermediate formable in the presence of peroxide or molecular oxygen, and measuring chemiluminescence therefrom to assay the analyte.

18. An assay for the presence of an analyte in a sample comprising contacting an analyte with the chemiluminescent-labeled specific binding material of claim 16, inducing chemiluminescence by decay of an intermediate formable in the presence of peroxide or molecular oxygen, and measuring chemiluminescence therefrom to assay the analyte.

* * * * *